United States Patent [19]

Turner

[11] 4,303,726

[45] Dec. 1, 1981

[54] METHODS AND COMPOSITIONS FOR PRESERVATION OF TIMBER

[75] Inventor: John H. W. Turner, Chapel en le Frith, England

[73] Assignee: Manchem Limited, Manchester, England

[21] Appl. No.: 162,820

[22] Filed: Jun. 25, 1980

[30] Foreign Application Priority Data

Jun. 25, 1979 [GB] United Kingdom ............ 22049/79

[51] Int. Cl.³ .................... B05D 1/18; B05D 3/00; C09D 5/14
[52] U.S. Cl. .................... 427/297; 106/15.05; 106/18.3; 106/18.36; 424/148; 424/154; 427/397; 427/440; 428/541; 428/907
[58] Field of Search ............. 427/297, 440, 397; 106/18.3, 18.36, 15.05; 424/148, 154; 428/541, 907

[56] References Cited

U.S. PATENT DOCUMENTS 2,216,775 10/1940 Helson ............................ 427/298
3,877,979 4/1975 Clark ............................ 106/18.3 X
4,234,340 11/1980 Pellico ......................... 106/18.36 X

FOREIGN PATENT DOCUMENTS 972804 10/1964 United Kingdom .

*Primary Examiner*—Michael R. Lusignan
*Attorney, Agent, or Firm*—J. R. Thornton

[57] ABSTRACT

Fungicidal compositions comprising at least one organometallic compound of aluminum and/or boron, at least one divalent metal and at least one carboxylic acid group. The compositions are useful in preserving timber.

10 Claims, No Drawings

METHODS AND COMPOSITIONS FOR PRESERVATION OF TIMBER

This invention relates to timber preservation and more particularly relates to fungicidal compositons containing aluminum and/or boron and their use in preserving timber.

The fungicidal compositions of this invention comprise at least one metal-organic compound which contains aluminum and/or boron, at least one divalent metal element or metal radical, the aluminum and/or boron atom and the divalent atom or atoms being linked through oxygen atoms, and at least one carboxylic acid radical, together with a suitable carrier therefor.

The method according to the invention achieves protection of timber against wood-decaying fungi such as *Coniophera puteana.*

Acccording to this invention, the fungicidal compositions may be introduced into the timber by any of the well known processes which ensure that the fungicide is uniformly distributed throughout the timber.

The fungicidal compositions are preferably uniformly distributed throughout the timber by means of vacuum impregnation, and sawn timber is particularly advantageously preserved by the method according to the invention.

The metal-organic compounds used in the method according to the invention and processes for their preparation are disclosed and claimed in U.K. Pat. No. 972,804.

Compounds containing boron are preferred for use in the fungicidal compositions used in the method according to the invention.

The carboxylic acid radicals are preferably derived from carboxylic acids containing eight to ten carbon atoms. It has been found that the neodecanoic acid (Versatic 10) radical is particularly suitable on account of its good solubility and ease of processing.

A particularly preferred compound for use in the method according to the invention is zinc boron versatate.

Suitable carriers in which the metal-organic compounds are dissolved are organic solvents, preferably hydrocarbons and more preferably white spirit.

Previously proposed fungicidal compositions have usually contained not less than about 2 to 3% by weight based on the total weight of composition of divalent metal to ensure adequate protection of timber in all environmental conditions over a long period of time. Employing the compositions of the present invention, much less metal is required to give adequate protection. This is particularly important for timber which is exposed to heavy rainfall since metal soaps may slowly leach through wet timber.

It has further been found that the fungicidal effect of the compounds used in the method according to the invention can be further enhanced by incorporating one or more substituted phenols of known fungicidal activity, for example, o-phenylphenol, nonylphenol and chlorinated phenols.

Thus, according to another aspect, the invention provides a fungicidal composition comprising at least one metal-organic compound which contains aluminum and/or boron, at least oe divalent metal element or metal radical, the aluminum and/or boron atom and the divalent atom or atoms being linked through oxygen atoms, and at least one carboxylic acid radical, and one or more substituted phenols together with a suitable carrier therefor.

It has been found that the use of divalent metals in the form described herein results in increased fungicidal activity as compared with conventional compounds such as copper and zinc naphthenate.

Apart from the increased fungicidal activity, two other advantages arise from the use of divalent metals in the form described herein. These are that greatly reduced amounts of fatty acid are required to solubilize the metal, and also that much higher concentrations of metal in solution in solvents such as hydrocarbon solvents can be obtained than is possible with the normal di-soaps of the metals with naphthenic or with synthetic fatty acids.

The present invention will be further illustrated by reference to a series of tests comparing the fungicidal properties of compositions of the present invention with a known commerically available fungicide used for treating timber.

The compositions which comprised zinc boron versatate or zinc naphthenate (comparison) dissovled in white spirit in different concentrations were subjected to a series of tests, described below, using blocks of Scots pine (Pinus Sylvestris) sapwood which were subjected to infestation by the wood destroying fungus *Coniophera putenana.*

EXAMPLE 1

Wood blocks sized 14.5×10×7 mm, were oven dried for 18 hours, cooled and weighed. They were then transferred to a glass vessel which was evacuated of air down to a pressure of less than 10 mm. of mercury and were then held at this pressure for 10 minutes. The fungicidal treating solution was then admitted to the vessel to cover the blocks which were left covered for two hours to ensure full and uniform impregnation. The blocks were removed from the solution, allowed to drain and then reweighed to determine the uptake of the fungicidal treating compound. The blocks were then allowed to dry slowly for three weeks and then were sterilized by exposure to 1,2-expoxypropane vapor followed by ventilation in sterile air. The blocks were then transferred aseptically to actively growing soil feeder block cultures of *Coniophera puteana* and incubated for six weeks at 22° C. At the end of this period the extent of overgrowth on the test blocks was noted. The blocks were removed from the culture, oven dried and reweighed so that the loss in mass of each block due to fungal decay could be noted.

From ther series of tests conducted, it was possible to determine the toxic limits for the individual treating compounds, such toxic limits being defined as the interval between the concentration or loading which just permits decay and the next higher concentration which inhibits all decay the following results were obtained:

| Compound | Toxic limits % w/w Zn in treating solution | Toxic limits Kg Zn/m$^3$ wood |
|---|---|---|
| Zinc naphthenate (comparative) | 0.63–1.00 | 2.80–4.50 |
| Zinc Boron Versatate | 0.25–0.40 | 1.05–1.80 |

It may be seen that the quantity of zinc required to prevent growth of *Coniophera puteana* is very significantly reduced when applied in the form of the zinc boron versatate rather than as zinc naphthenate.

Further tests were carried to where the treated wood blocks were subjected to a water leaching process prior to infestation to simulate conditions where the fungicides may be required to protect timber which is exposed to adverse weather conditions.

EXAMPLE 2

Wood blocks, sized 14.5×10×7 mm, were impregnated with fungicidal compositions as described in Example 1 and allowed to dry slowly for three weeks. The blocks were then leached in deionized water according to the following procedure:

The treated wood blocks were vacuum impregnated with water and allowed to soak for two hours. The water was then poured away and a further 30 ml. was added. The water was changed after 24 hours and 48 hours and thereafter at a minimum interval of 24 hours and a maximum of 72 hours until the water had been changed on a total of 10 occasions. The blocks were then placed in a well ventilated oven at 45° to 50° C. in order to dry to a moisture content of about 20% by weight. The blocks were then sterilized and exposed to cultures of *Coniophera puteana* as described in Example 1.

The leaching process did in most cases cause some redution in fungicidal activity, but the retained activity of the fungicidal compositions of the present invention was never inferior and in certain cases was superior to the corresponding comparative metal naphthenate compositions.

Further tests were carried out using iron boron versatate both in the unoxidized and oxidized form and manganese boron versatate.

EXAMPLE 3

Each compound was dissolved in a 50/50 w/w mixture of toluene and hexane to give solution concentrations by weight of 2.2, 1.0, 0.22 and 0.10% metal. Blocks of Scots pine (*Pinus sylvestris*) sapwood, 14.5×10×7 mm were dried in an oven at 105° C. for 18 hours, cooled weighed, Sets of six of these blocks were placed in glass vessels, weighted down with glass weights and then evacuated to a pressure of less than 10 mm. Hg and held for 10 minutes. The treatment solution was then slowly admitted to the vessel until the blocks were covered with liquid. Air was then admitted to the vessel and the blocks were left for 2 hours to permit full and uniform impregnation with solution. The blocks were reweighed to determine the uptake of solution and thus the loading of metal.

The blocks were allowed to dry slowly for three weeks, after which four of each set of six were sterilized with 1,2-epoxypropane vapor for 24 hours and then ventilated in sterile air for 72 hours. The blocks were then transferred aseptically to actively growing soil feeder block cultures of *Coniophera puteana* and incubated for six weeks at 22° C. After this period the culture vessels were examined and the extent of overgrowth on the test blocks noted. The blocks were removed from culture, any adhering mycelium scraped off and the blocks weighed, oven dried and reweighed so that the loss in weight of each block due to fungal decay could be calculated. The following results were obtained:

| Compound | Toxic limits | |
|---|---|---|
| | % w/w metal in treating solution | kg metal/m³ wood |
| Manganese boroversatate | 0.47–1.0 | 1.80–4.05 |
| Iron boroversatate, unoxidized | 0.47–1.0 | 2.00–4.30 |
| Iron boroversatate, oxidized | 0.47–1.0 | 1.80–3.65 |

Various changes and modifications of the invention can be made, and to the extent that such variations incorporate the spirit of this invention, they are intended to included within the scope of the appended claims.

What is claimed is:

1. A method of preserving timber which comprises impregnating timber with a funicidal composition comprising at least one metal-organic compounds which contains aluminum and/or boron, at least one divalent metal element or metal radical, the aluminum and/or boron atom and the divalent metal atom or atoms being linked through oxygen atoms, and at least one carboxylic acid radical, together with a suitable carrier therefor.

2. A method according to claim 1, wherein said at least one metal organic compound contains boron.

3. A method according to claim 1, wherein the carboxylic acid radical contains eight to ten carbon atoms.

4. A method according to claim 1, wherein the said at least one metal organic compound is zinc boron versatate.

5. A method according to claim 1, wherein the timber is impregnated by vacuum impregnation.

6. A method according to claim 1 in which said composition contains a fungicidal phenol selected from the group consisting of o-phenylphenol, nonylphenol and chlorinated phenols.

7. A timber impregnating composition comprising at least one metal-organic compound which contains aluminum and/or boron, at least one divalent metal element or metal radical, the aluminum and/or boron atom and the divalent metal atom or atoms being linked through oxygen atoms, and at least one carboxylic acid radical, one or more fungicidal phenols selected from the group consisting of o-phenylphenol, nonylphenol and chlorinated phenols, and a hydrocarbon solvent therefor.

8. A timber impregnating composition according to claim 7, wherein the at least one metal organic compound contains boron.

9. A timber impregnating composition according to claim 7, wherein the carboxylic acid radical contains eight to ten carbon atoms.

10. A timber impregnating composition according to claim 7, wherein the at least one metal organic compound is zinc boron versatate.

* * * * *

UNITED STATES PATENT OFFICE
CERTIFICATE OF CORRECTION

Patent No. 4,303,726                    Dated December 1, 1981

Inventor(s)    John Harry Wallice Turner

It is certified that error appears in the above-identified patent and that said Letters Patent are hereby corrected as shown below:

Column 1, line 65, the word "oe" should read -- one -- .

Column 2, line 22, the word "dissovled" should read -- dissolved -- .

Column 2, line 43, the word "expoxypropane" should read -- epoxypropane -- .

Column 2, line 52, the word "ther" should read -- the -- .

Column 3, line 43, the words "cooled weighed" should read -- cooled and weighed -- .

Column 4, line 18, the words "to included" should read -- to be included -- .

Column 4, line 22, the word "funicidal" should read -- fungicidal -- .

Column 4, line 23, the word "compounds" should read -- compound -- .

Signed and Sealed this

Sixteenth Day of February 1982

[SEAL]

Attest:

GERALD J. MOSSINGHOFF

Attesting Officer    Commissioner of Patents and Trademarks